(12) United States Patent
Rothstein et al.

(10) Patent No.: US 9,050,129 B2
(45) Date of Patent: Jun. 9, 2015

(54) AUTO-CLOSURE APICAL ACCESS POSITIONER DEVICE AND METHOD

(75) Inventors: Paul T. Rothstein, Elk River, MN (US); Alexander J. Hill, Blaine, MN (US); Michael J. Hobday, Lino Lakes, MN (US); Michael M. Green, Forest Lake, MN (US); Paul A. Iaizzo, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 753 days.

(21) Appl. No.: 12/750,829

(22) Filed: Mar. 31, 2010

(65) Prior Publication Data
US 2010/0274091 A1 Oct. 28, 2010

Related U.S. Application Data

(60) Provisional application No. 61/172,256, filed on Apr. 24, 2009.

(51) Int. Cl.
*A61B 17/34* (2006.01)
*A61B 17/064* (2006.01)
*A61B 17/068* (2006.01)
*A61B 19/00* (2006.01)
*A61B 17/00* (2006.01)
*A61B 17/30* (2006.01)

(52) U.S. Cl.
CPC .......... *A61B 17/3423* (2013.01); *A61B 17/064* (2013.01); *A61B 17/068* (2013.01); *A61B 19/5202* (2013.01); *A61B 2017/00022* (2013.01); *A61B 2017/00243* (2013.01); *A61B 2017/00575* (2013.01); *A61B 2017/306* (2013.01); *A61B 2017/3425* (2013.01); *A61B 2017/3488* (2013.01)

(58) Field of Classification Search
CPC .............. A61B 2017/0237; A61B 2017/0243; A61B 2017/0212; A61B 2017/0225; A61B 2017/3425; A61B 17/0218
USPC .................. 600/201, 204, 210, 227; 606/108
See application file for complete search history.

(56) References Cited

U.S. PATENT DOCUMENTS

| | | | |
|---|---|---|---|
| 6,558,314 B1* | 5/2003 | Adelman et al. | 600/37 |
| 2002/0058856 A1* | 5/2002 | Peng et al. | 600/37 |
| 2004/0153098 A1* | 8/2004 | Chin et al. | 606/129 |
| 2005/0038316 A1 | 2/2005 | Taylor | |
| 2007/0123840 A1* | 5/2007 | Cox | 604/514 |
| 2008/0161826 A1* | 7/2008 | Guiraudon | 606/108 |

FOREIGN PATENT DOCUMENTS

| | | | | |
|---|---|---|---|---|
| WO | 2005/044079 | 5/2005 | | |
| WO | 2008/044147 | 4/2008 | | |
| WO | WO 2008044147 A2 * | 4/2008 | ............. | A61B 17/34 |

* cited by examiner

*Primary Examiner* — Eduardo C Robert
*Assistant Examiner* — Julianna N Harvey

(57) ABSTRACT

A positioning device for providing access to a ventricle of a heart. In one embodiment, the device includes a cup positionable over an apex of the heart and at least a first access valve in the cup for accessing an entry point to the ventricle of the heart.

19 Claims, 16 Drawing Sheets

AUTO-CLOSURE APICAL ACCESS POSITIONER DEVICE AND METHOD

CROSS REFERENCE TO RELATED APPLICATION

This application claims the benefit under 35 U.S.C. §119(e) of U.S. Provisional Patent Application No. 61/172,256, filed Apr. 24, 2009, which is incorporated herein by reference in its entirety.

TECHNICAL FIELD

The invention is directed to heart repair procedures. In particular, a method and device are disclosed for completing a minimally invasive repair or replacement procedure in a ventricle of the heart.

BACKGROUND

Accessing a ventricle of the heart can be necessary for a number of procedures including, for example, mitral or aortic valve repair or replacement, or repair of an atrial or ventricular septal defect. There are multiple methods for completing such procedures, however many such methods involve cardiopulmonary bypass. In particular, open chest, sternotomy bypass methods are currently preferred for many such operations. Such sternotomy methods, however, may exclude certain patient populations including those with comorbidities (obesity, diabetes, bleeding disorders) that may significantly impact survival rates during such procedures. Such risk may be so high that surgeons may choose not operate on such patients.

Moreover, the ability to stabilize a beating heart and allow hemostatic access via the apex of the heart may effectively allow the physician to perform repairs to the heart. In some procedures, such as transapical aortic valve implantation, device placement may be more accurate than percutaneous transfemoral procedures. Additionally, non-sternotomy methods such as a subxyphoid approach may provide a less traumatic procedure for the patient than sawing through their sternum.

Accordingly, improved devices/methods of accessing a ventricle of the heart are desirable. In particular, procedures that do not require a sternotomy or that the patient be placed on bypass are needed.

SUMMARY

In one aspect of the invention, a positioning device is described for providing access to a ventricle of a heart. In one embodiment, the positioning device includes a cup positionable over the apex of the heart and at least a first hemostatic access valve in the cup for hemostatically accessing an entry point to the ventricle of the heart. Preferably, the cup can be a suction cup that attaches to the apex of the heart to allow positioning of the apex within a chest cavity. Additionally, the hemostatic access valve may be positioned outside of the closed chest of a patient. In this way, advantageously, the apex of the heart may be more readily accessed in a closed chest procedure. Additionally, the patient may not need to be placed on bypass.

In another aspect of the invention, a method of accessing a ventricle of the heart is provided, which includes placing a cup portion of a positioning device at the apex of the heart, forming an entry point into a ventricle of the heart through a hemostatic valve in the cup portion of the positioning device, and hemostatically accessing the ventricle of the heart through the hemostatic valve and entry point.

Additionally, in another embodiment, the positioning device can house one or more needles, each needle housing at least one clip. To close a ventricle entry point after a procedure, the needles may be advanced into the wall of the heart radially around the entry point and shifted radially inwards to close the entry point. The clips may then be deployed into the heart to hold the entry point closed.

In another embodiment, clips are formed from a super-elastic shape memory alloy such as, for example, Nitinol. Alternatively, the clips may be made of a bioabsorbable or non-alloy material. Biocompatible super-elastic materials may also be utilized. A super-elastic metal is sometimes known as a shape memory alloy (also, smart metal, memory alloy or muscle wire) that remembers its shape and can be returned to that shape after being deformed, such as by applying heat to the alloy or removing an applied stress from the alloy, for example. As the stress is removed, the material may undergo a martenisitic to austenitic conversion and spring back (e.g., self-revert) to its original or undeformed or undeflected configuration. In alternative embodiments, a biocompatible elastic material such as stainless steel may be utilized for the clips.

BRIEF DESCRIPTION OF THE DRAWINGS

The present invention will be further explained with reference to the appended Figures, wherein like structure is referred to by like numerals throughout the several views, and wherein.

DETAILED DESCRIPTION

In the following description, for the purposes of explanation, numerous specific details are set forth in order to provide a thorough understanding of the invention. It will be evident, however, to one skilled in the art that the exemplary embodiments may be practiced without these specific details. In other instances, structures and device are shown in diagram form in order to facilitate description of the exemplary embodiments.

A device and method for access to a ventricle of a heart is described. The device and method advantageously allow hemostatic access to a heart ventricle during either sternotomy or non-sternotomy procedures and provide for closure of an entry point after a procedure is completed. Additionally, the heart may not need to be placed on bypass during such procedures when using the devices of the invention.

Figure 1:
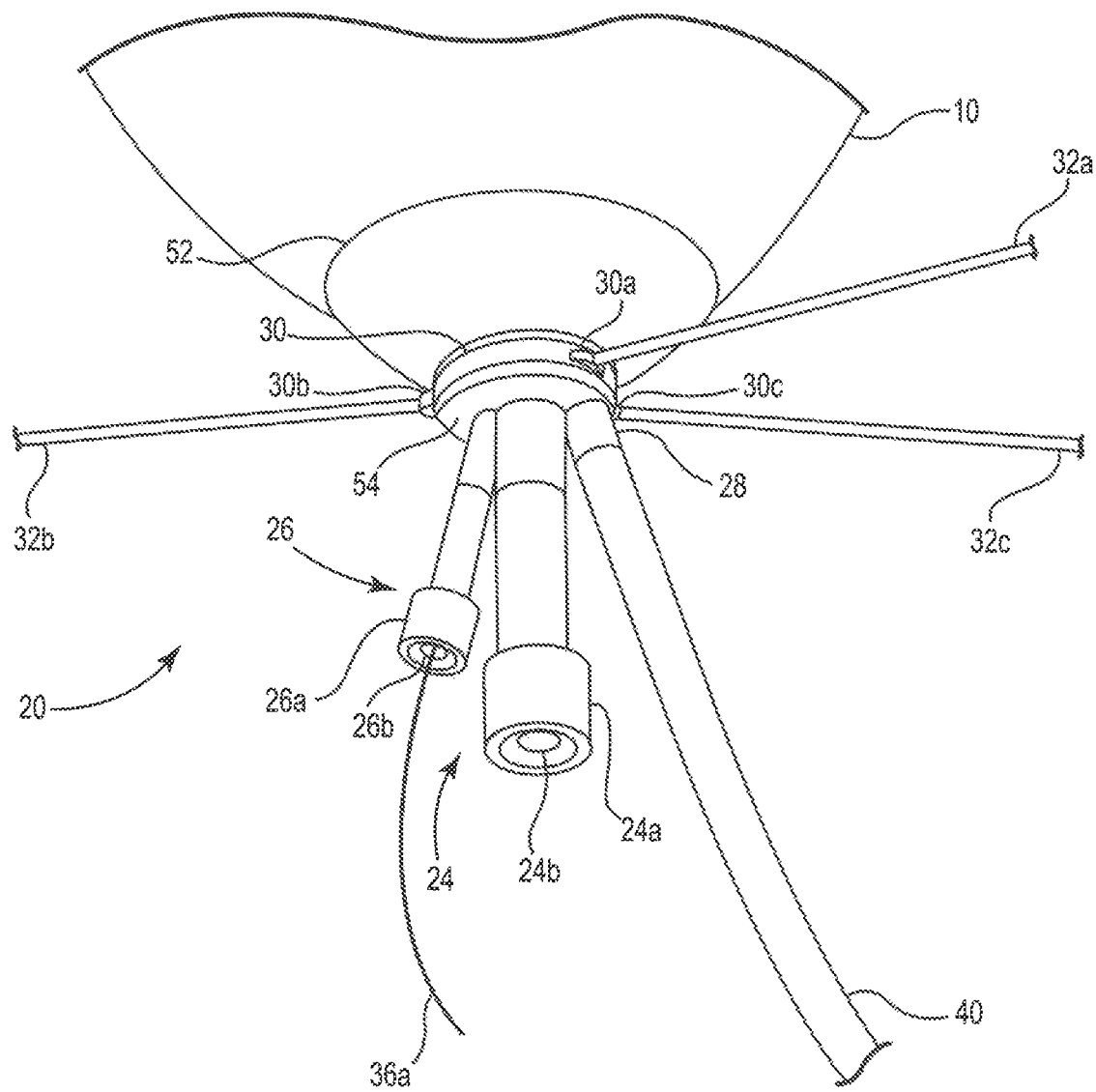
FIG. 1 is an oblique drawing illustrating one embodiment of a positioning device for providing apical heart access in accordance with the invention.

FIG. 1 illustrates one embodiment of a positioning device 20 for providing hemostatic access to an apex of the heart 10 in accordance with the invention. In the embodiment of FIG. 1, positioning device 20 includes a relatively dome-shaped or semi-circular suction cup 52 having a cylindrical base 54 formed in a central section of suction cup 52. The suction cup 52 can be made of a relatively flexible material formed into a curved three-dimensional shape. This shape may include a flat open face which, when pressed against a flat surface, would adhere to that surface due to the lower pressure between the flexible material and the flat surface as compared to the pressure outside the flexible material. It is not required, however, that the material from which the suction cup is made is deformable in this manner, and it is possible that it is instead formed from material that is at least slightly stiff or rigid. In this Figure, the suction cup 52 is shown as being positioned at an apical tip of heart 10, although it is understood that it can be used in a different position relative to a different area of the heart or another area of a patient. Suction cup 52 of positioning device 20 can act as a stabilizer that holds positioning device 20 in a desired location relative to heart 10; however, it is also possible the suction cup can have a different shape than that shown, such as may be designed or selected to have an internal shape that matches the outer shape of the location where it will be positioned. For example, a cup-shaped or non-cup shaped structure can be used that does not provide suction, or another stabilization mechanism for attachment to the apex of a heart or other location may be used. For example, direct pressure can be placed on positioning device 20 or another mechanical attachment device or system may be positioned at the interior of a structure to stabilize positioning device 20 at the apex of heart 10.

In the embodiment of FIG. 1, base 54 includes a first access valve 24 and second access valve 26 protruding from an exterior face thereof. Access valves 24 and 26 are preferably hemostatic. First access valve 24 and second access valve 26 each include cylindrical flanges 24a and 26a, respectively, which are provided at distal ends thereof. Additionally, as explained further below in association with FIG. 2, first access valve 24 and second access valve 26 each include cylindrical channels 24b and 26b, respectively, which pass from the distal ends thereof to an interior region of suction cup 52. Although the embodiment of positioning device 20 shown in FIG. 1 includes two access valves (24 and 26), a positioning device in accordance with the invention may include only one or more than two access valves. Additionally, the lengths and outer diameters of access valves 24 and 26, and the diameters of channels 24b and 26b may be varied, depending on their desired use. Positioning device 20 also includes a vacuum port 28 extending from base 54 adjacent to access valves 24 and 26. A vacuum supply tube 40 can extend from vacuum port 28 to provide suction at an interior region of suction cup 52.

During a procedure on heart 10, at least a portion of first access valve 24, second access valve 26, and vacuum supply tube 40 may be positioned outside the chest of a patient. In particular, the flange 24a of first access valve 24, the flange 26a of second access valve 26, and the distal portion of vacuum supply tube 40 may be positioned outside the chest of a patient. In this way, access to a ventricle in heart 10 can be achieved in a non-sternotomy procedure on heart 10.

In the embodiment of FIG. 1, positioning device 20 additionally includes a swivel ring 30 placed circumferentially around the outside of base 54. Swivel ring 30 is preferably free to rotate circumferentially about base 54. In the embodiment of FIG. 1, swivel ring 30 includes three suture anchors 30a, 30b, and 30c. As explained further below, sutures 32a, 32b and 32c may be passed through suture anchors 30a, 30b and 30c to allow positioning device 20 to be appropriately located and stabilized at the apex of heart 10. Further, although the embodiment shown in FIG. 1 uses swivel ring 30 in conjunction with sutures 32a, 32b, and 32c to position the positioning device 20, it is also considered that a rigid rod, articulating arm, or other device connected to positioning device 20 could also be used to position positioning device 20 relative to heart 10. Also, while positioning device 20 is shown as using suction cup 52 in conjunction with sutures 32a, 32b and 32c, it is understood that sutures 32a, 32b and 32c may be used without suction cup 52, or that suction cup 52 may be used without sutures 32a, 32b and 32c.

Figure 2:
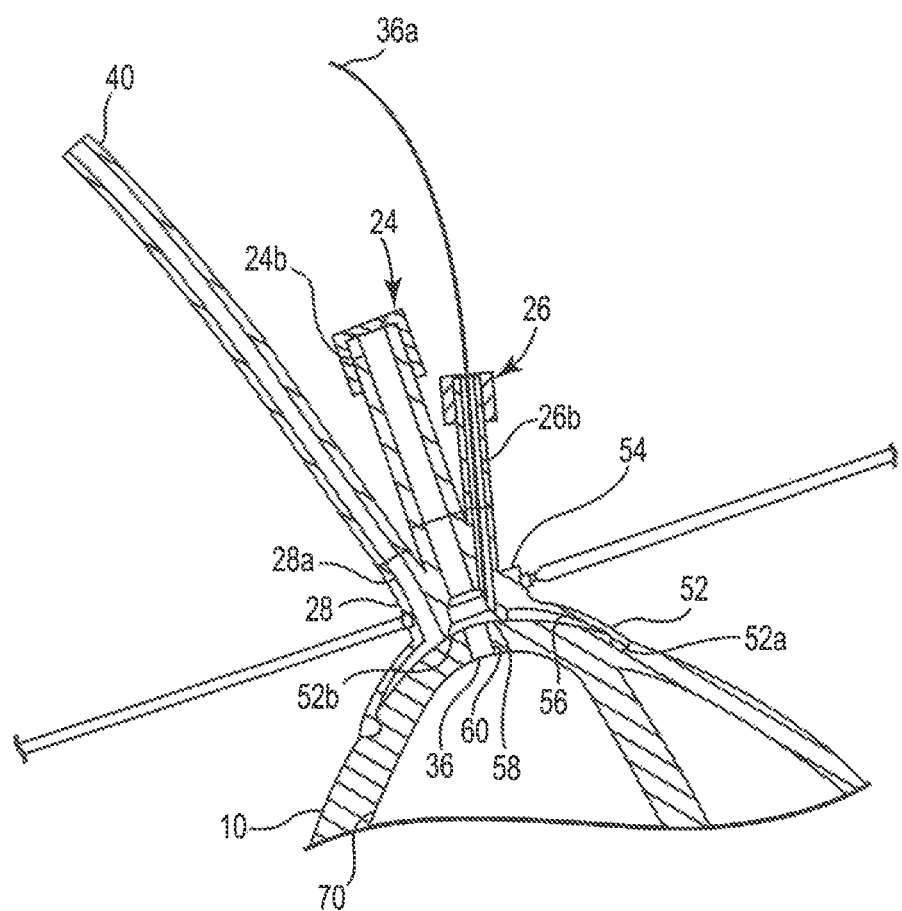
FIG. 2 is a sectional view of the positioning device shown in FIG. 1.

FIG. 2 is a sectional view of positioning device 20 illustrating one embodiment of an internal structure thereof. As shown, an interior of suction cup 52 includes a thickened, circular outer rim 52a and a circular inner rim 52b concentrically located inside outer rim 52a. Inner rim 52b preferably has a triangular shaped cross-section with one corner of the triangle protruding from an interior surface of suction cup 52 that can be used to contact an outer surface of heart 10. Additionally, outer rim 52a also protrudes from an inner surface of suction cup 52 for contact with heart 10. In this way, outer rim 52a and inner rim 52b can each form a seal, which may preferably be substantially airtight, between suction cup 52 and an outer surface of heart 10. Additionally, outer rim 52a and inner rim 52b define a concentrically located toroidal trough 56. Also as shown in FIG. 2, vacuum port 28 includes an interior channel 28a that is open to toroidal trough 56. Because outer rim 52a and inner rim 52b substantially form a seal between suction cup 52 and an outer surface of heart 10, a vacuum can be formed in toroidal trough 56 against an outer surface of heart 10 by providing suction at vacuum port 28 via vacuum supply tube 40. Such vacuum created in toroidal trough 56 acts to secure positioning device 20 against the outer surface of heart 10.

Inner rim 52b of suction cup 52 also preferably forms a circular trough 58 at an interior (or heart side) of suction cup 52 that is separated from toroidal trough 56 by inner rim 52b. As shown in FIG. 2, circular trough 58 is open to channel 24b of access valve 24. Because circular trough 58 is separated from toroidal trough 56, any vacuum generated in toroidal trough 56 will not be lost through channel 24b. In this way, access can be provided through channel 24b of first access valve 24 to the apex of heart 10. As discussed further below, this allows the creation of an entry point 60 in the apex of heart 10 by guiding a needle or other puncturing device through channel 24b. This additionally allows access by other devices to the apex of heart 10 for performing procedures inside a ventricle thereof. Further, because first access valve 24 is preferably hemostatic, substantially hemostatic access can be provided by positioning device 20 relative to an entry point 60 in heart 10.

In the embodiment shown in FIG. 2, channel 26b of second access valve 26 is also open to circular trough 58. This can allow an additional place for access by various devices to the apex of heart 10. Additionally, as shown in FIG. 2, and as discussed further below, purse string sutures 36 for closing entry point 60 in can be placed in the wall of heart 10 around entry point 60 as is understood by one of ordinary skill. Purse string suture tail 36a can then be threaded through channel 26b of second access valve 26 for closing entry point 60 after a procedure is completed but before removing positioning device 20. Like first access valve 24, second access valve 26 is also preferably hemostatic.

Figure 13:
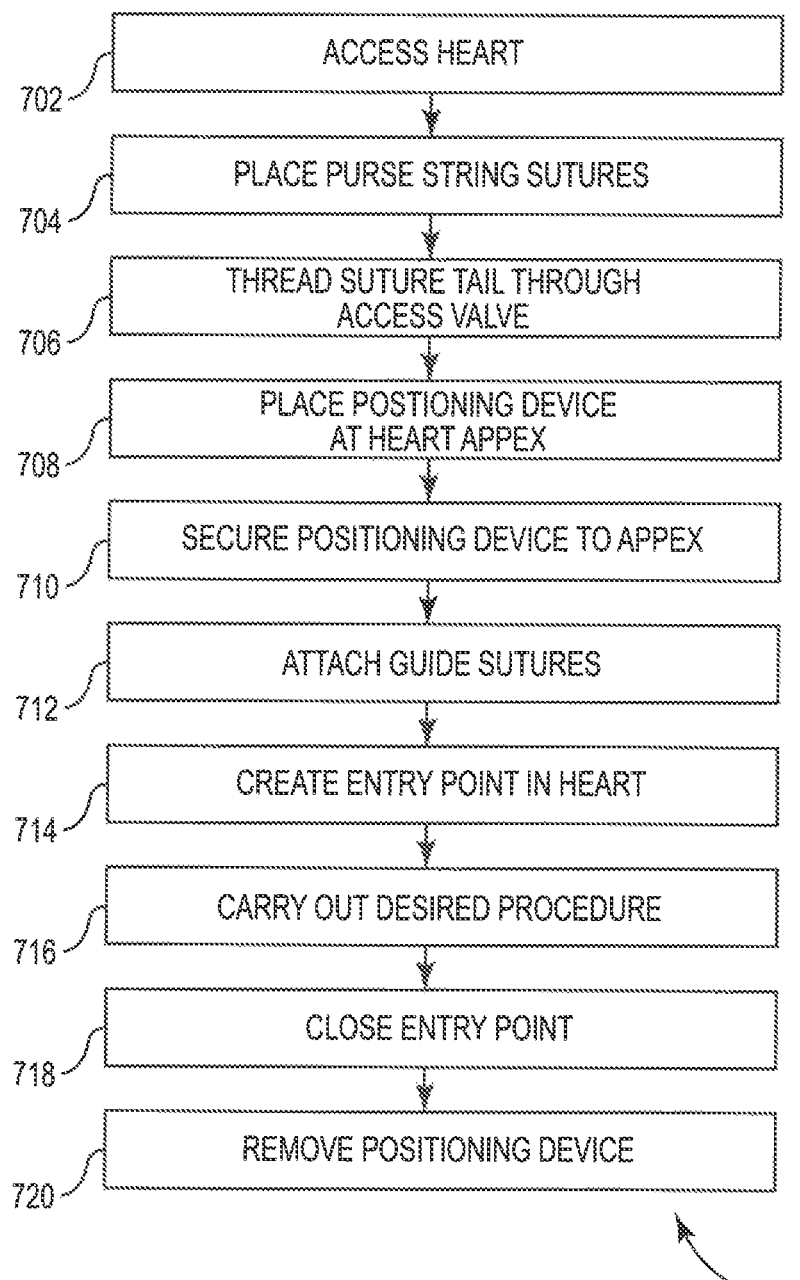
FIG. 13 is a flow chart illustrating one embodiment of a method accessing a ventricle of a heart, in accordance with the invention.

Referring to FIGS. 1, 2 and 13, one exemplary embodiment of a method 700 of accessing the apex of a heart in accordance with the invention is illustrated. In a first step 702 of the process, access is first gained to the apex of the heart. This can be done in any conventional manner including, but not limited to, a mini-thorocotomy or a sub-xiphoid incision. In step 704, one or more purse string sutures 36 can be placed in an area around the desired entry point 60 into a ventricle of the heart. Purse string sutures 36 will be used to close entry point 60 when the desired procedure is completed. Placement of such purse string sutures 36 is understood by one of ordinary skill in the art. In step 706, a purse string suture tail 36a can be threaded through channel 26b of second access valve 26 of positioning device 20. Purse string suture tail 36a may also be threaded through channel 24b of primary access valve 24 if secondary access valve 26 is used for another purpose or is not available. In step 708, positioning device 20 can be guided through the body opening (not shown) providing access to heart 10 and positioned against the apex of the heart. A standard grasper, or other suitable device, may be used to accomplish this.

Once positioned against the heart apex, suction can be activated through vacuum supply tube 40 to hold positioning device 20 against the heart apex, as in step 710. In step 712, guide sutures may be attached to their desired locations. For one example, three guide sutures 32a, 32b and 32c (shown in FIG. 1) may be placed through three separate intercostal locations (not shown) and threaded through suture anchors 30a, 30b and 30c (also shown in FIG. 1). In this way, the positioning device may be optimally located to place an entry point through the heart wall into a ventricle thereof. Because suction cup 52 is stably attached to apex of heart 10, the apex can be shifted inside the chest cavity to allow flanges 24a and/or 26a of first and second access valves 24 and 26, respectively, to be outside the chest cavity of a patient. In this way, the apex of heart 10 is easily accessible through first and second access valves 24 and 26 in a non-sternotomy procedure.

Figure 3A:
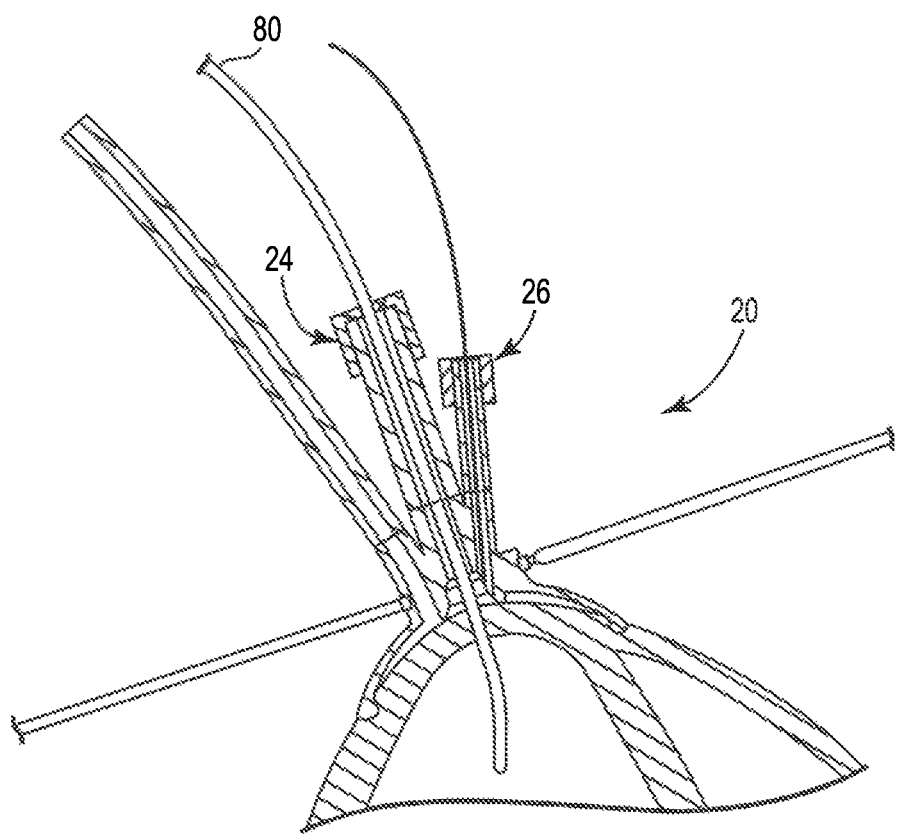
FIG. 3A is a sectional view of the positioning device shown in FIG. 1 including a catheter accessing a ventricle of a heart.
Figure 3B:
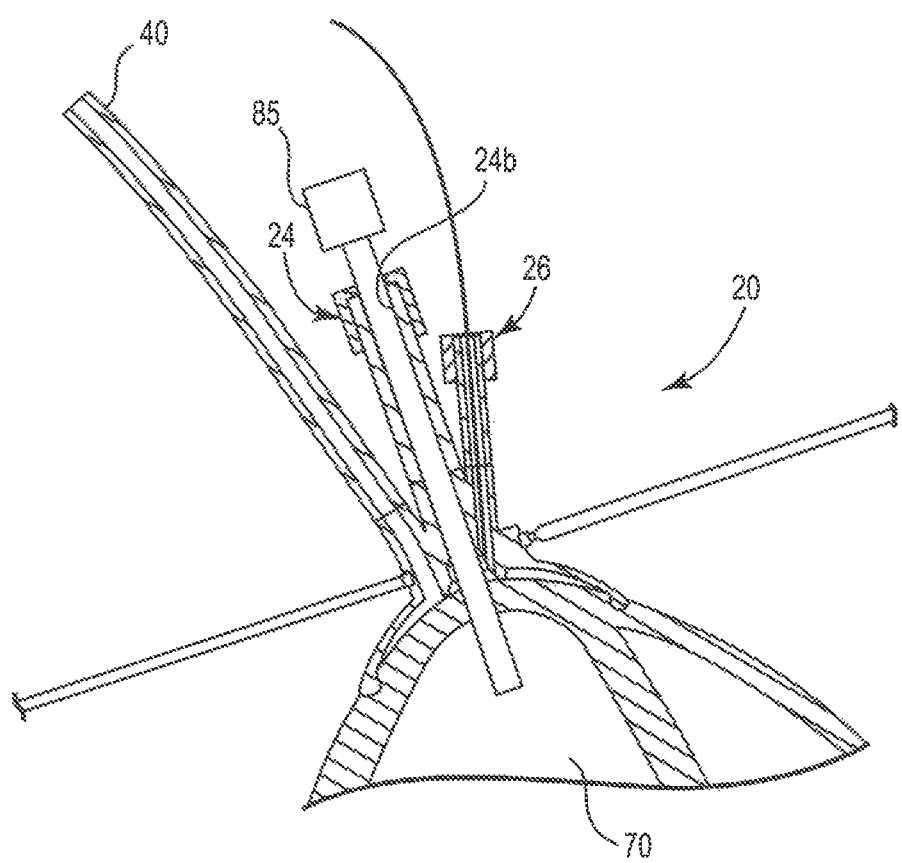
FIG. 3B is a sectional view of the positioning device shown in FIG. 1 including an introducer or port for accessing a ventricle of a heart.

Once positioning device 20 is appropriately located, a puncturing apparatus, such as a needle followed by a dilator, may be used to create entry point 60 in the heart apex, as in step 714. Entry point 60 would advantageously be hemostatically isolated and could be used to guide a catheter 80 or other device through channel 24b of first access valve 24 into left ventricle 70 to perform a procedure therein, as in step 716 and as is illustrated in FIG. 3B. Additionally, as shown in FIG. 3B, a substantially rigid introducer or port 85 can be guided through channel 24b of first access valve 24 into left ventricle 70 to facilitate easier insertion and retraction of devices or, as discussed below, introduction of one or more drugs into a ventricle of heart 10. After completing any procedure to be carried out, any implements may be removed from entry point 60 and positioning device 20 and the tail 36a of purse string sutures 36 may be drawn to close entry point 60, as in step 718. Positioning device 20 may then be removed from heart 10 by removing suction from vacuum supply tube 40 and cutting guide sutures 32a, 32b and 32c, as in step 720. Final tie-off of any sutures may be done after device removal.

Figure 4:
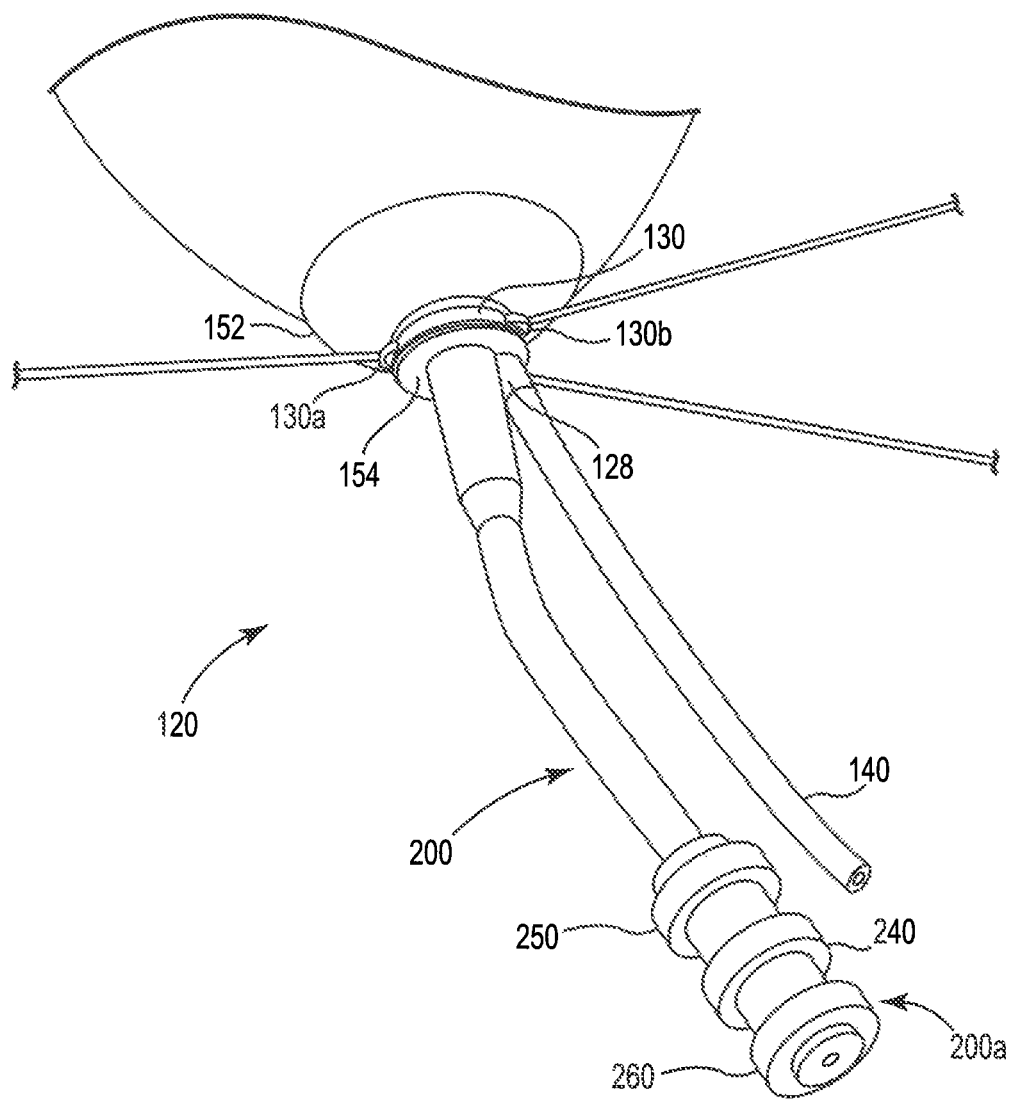
FIG. 4 is an oblique view of another embodiment of a positioning device for providing apical heart access in accordance with the invention.

FIG. 4 illustrates another embodiment of a positioning device 120 in accordance with the invention. Like positioning device 20 shown in FIGS. 1 and 2, positioning device 120 includes a cylindrical base 154 located in a central region of a circular suction cup 152. Preferably, a swivel ring 130 is circumferentially rotatable about cylindrical base 154 and includes three suture anchors, although only suture anchors 130a and 130b are visible in this illustration. It is contemplated, however, that more or less than three suture anchors can be provided on the swivel ring. Positioning device 120 also includes a vacuum port 128 protruding from base 154 for interconnecting with a vacuum supply tube 140.

In the embodiment shown in FIG. 4, positioning device 120 includes only a single access valve 200, though it is considered that positioning device 120 may include one or more additional access valves. A closing mechanism is housed within access valve 200 such that a second access valve is not necessary to provide access to a purse string suture. In the embodiment of FIG. 4, access valve 200 also includes a cylindrical flange 200a adjacent to its distal end and having three circular sliders: a push-rod slider 240, a needle insertion slider 250 and a needle compression slider 260, each of which will be discussed further below. Preferably, access valve 200 includes a flexible neck portion to allow for easy positioning thereof during use. Additionally, cylindrical flange 200a can advantageously remain outside of a chest cavity during a heart procedure carried out using positioning device 120, thereby allowing any such procedure to be completed without performing a sternotomy.

Figure 5:
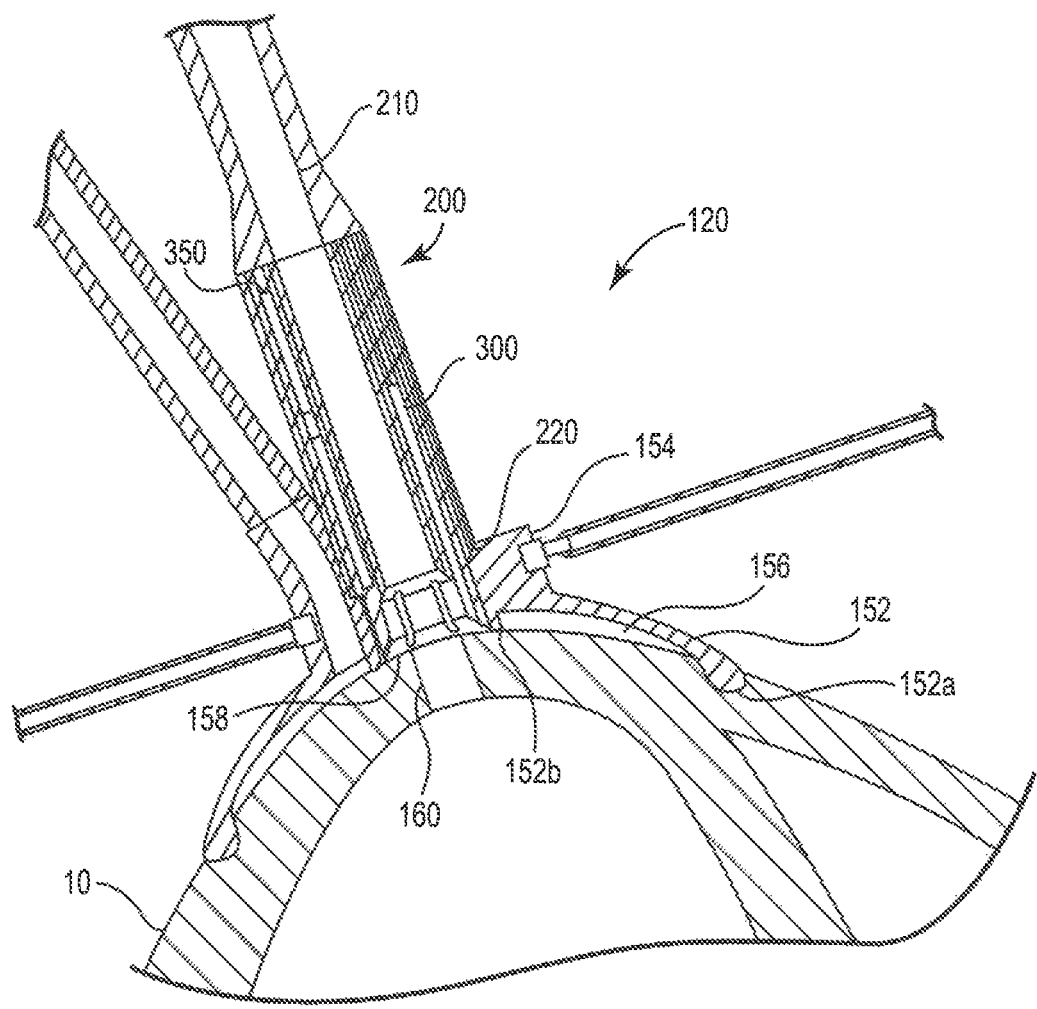
FIG. 5 is a sectional view of the positioning device shown in FIG. 4 illustrating a closure mechanism in accordance with the invention.

FIG. 5 is a sectional view of the embodiment of positioning device 120 illustrated in FIG. 4. As shown, the interior structure of suction cup 152 is relatively similar to that of suction cup 52 of positioning device 20 shown in FIGS. 1 and 2. In particular, suction cup 152 includes an outer rim 152a and an inner rim 152b that define a torroidal trough 156. In addition, a circular trough 158 is defined by the interior of inner rim 152b that facilitates hemostatic access to a ventricle of a heart 10 via an entry point 160. Additionally, access valve 200 includes a central channel 210 that is preferably open at one end to circular trough 158 and open at an opposite end (not shown) to the exterior of positioning device 120. In this way, hemostatic access is provided to a ventricle of heart 10 via entry point 160. Access valve 200 also includes a cylindrical channel 220 concentric with central channel 210. Cylindrical channel 220 passes through a base 154 of positioning device 120 and opens into circular trough 158. Cylindrical channel 220 can preferably house a needle assembly 300 and push rod assembly 350, which are illustrated in FIGS. 6A and 6B, respectively.

Figure 6A:
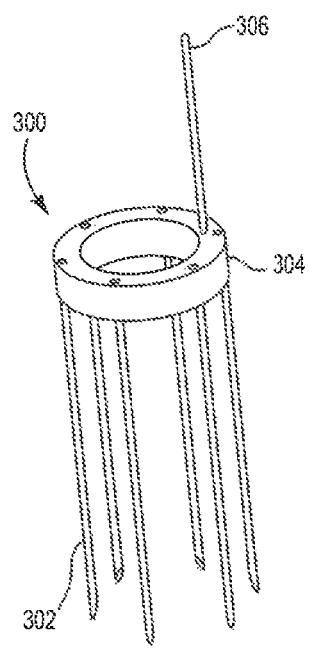
FIGS. 6A, 6B and 6C are oblique views of a needle assembly, a push-rod assembly, and a combination needle/push-rod assembly, respectively, each of which is for use in the closure mechanism shown in FIG. 5.

FIG. 6A is an oblique view of a needle assembly 300 in accordance with one embodiment of the invention. Needle assembly 300 includes a plurality of needles 302. Although the exemplary embodiment shown in FIG. 6A includes six needles, it is understood that any number of needles be included in needle assembly 300, and preferably six to eight needles are used. Needle assembly 300 also includes a needle manifold 304. Needle manifold 304 is a ring in which bases of needles 302 are fixed such that needles 302 protrude from manifold 304 in a circular pattern so that they are substantially parallel to one another. Needle assembly 300 also includes a needle push-pull wire 306 that is attachable through channel 220 (see FIG. 5) to needle insertion slider 250 shown in FIG. 4. As such, by sliding needle insertion slider 250 axially along flange 200a, needle assembly 300 and needles 302 are shifted axially along channel 220 and, as discussed below, can puncture the wall of heart 10 at the radial exterior of entry point 160 (see FIG. 5). Preferably, needles 302 are hollow and each houses a clip that, as explained below, can be operated to close entry point 160.

Figure 6B:
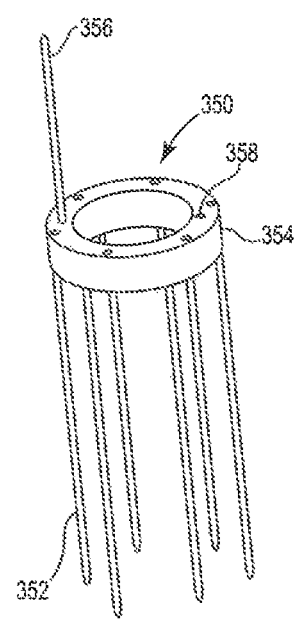

FIG. 6B is an oblique view of a pushrod assembly 350, which can also be positioned in cylindrical channel 220. According to this embodiment, pushrod assembly 350 is configured similarly to needle assembly 300 and includes a plurality of pushrods 352 spaced circumferentially around a ring shaped pushrod manifold 354. Although the exemplary embodiment shown in FIG. 6B illustrates a pushrod assembly that includes six pushrods, it is also understood that any number of pushrods can be included in pushrod assembly 350, and preferably six to eight pushrods are used. Additionally, in one exemplary embodiment, the pushrod assembly 350 includes the same number of pushrods as the number of needles included in the corresponding needle assembly 300 that is used in the same device. Pushrod assembly 350 further includes a push-pull wire 356 that is attachable through channel 220 (see FIG. 5) to push rod slider 240 shown in FIG. 4. As such, by sliding push-rod slider 240 axially along flange 200a, push rod assembly 350 and pushrods 352 can be shifted axially along channel 220.

Figure 6C:
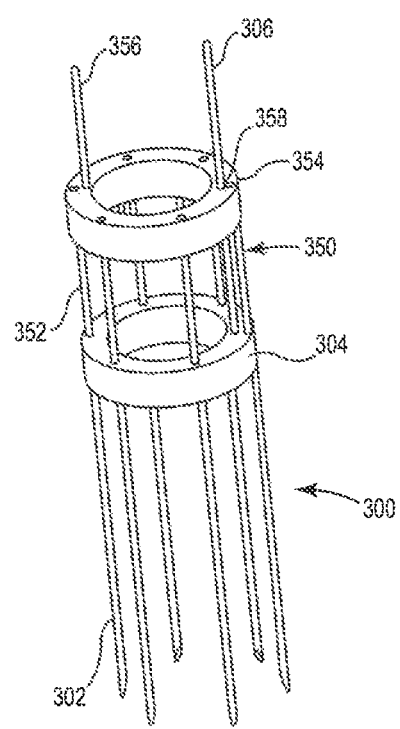

In this embodiment, push-rods 352 are sized and spaced around push-rod manifold 354 so that they are slideable into the hollow interior space of a corresponding needle 302, as is illustrated in FIG. 6C. In this embodiment, push-rods 352 are shown as being partially axially inserted into needles 302 so that push-rod manifold 354 is axially spaced from needle manifold 304. Additionally, in order to allow the needle assembly 300 to be manipulated by needle insertion slider 250, needle push-pull wire 306 is threaded though an axial opening 358 in push-rod manifold 354. In this way, one end of push-pull wire 306 can extend beyond the end of manifold 354 so that it is accessible for connection to the needle insertion slider 250 or another manipulation device.

Figure 7:
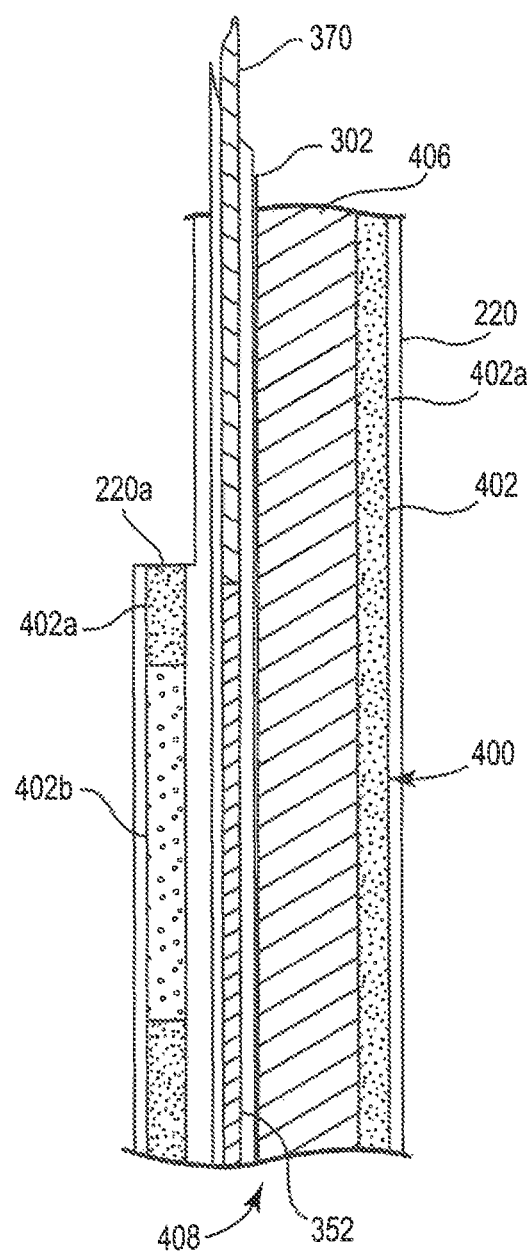
FIG. 7 is a close-up, sectional view of a portion of the closure mechanism shown in FIG. 5.

FIG. 7 is an enlarged, sectional view of a portion of positioning device 120 showing needle 302 as it can be positioned within a channel, such as channel 220. As shown, needle 302 has a push-rod 352 housed within its hollow interior space, wherein one end of push-rod 352 is abutted against a base of a clip 370. Additionally, FIG. 7 illustrates a compression sleeve 400 that is also positioned within channel 220. Compression sleeve 400 includes an inner section 406 that is preferably compressible or open and an outer wall 402 that includes a rigid section 402a and a compressible section 402b. Preferably, needle 302 is positioned in an axial channel through compression sleeve 400 so that needle 302 is positionable against an outer wall of channel 220. Additionally, compression sleeve 400 is preferably coupled to compression slider 260 on flange 200a (shown in FIG. 4). In this embodiment, sliding compression slider 260 axially towards base 154 of positioning device 120 will axially move a distal end 408 of compression sleeve 400 toward base 154 (see FIG. 5) of positioning device 120.

Figure 9:
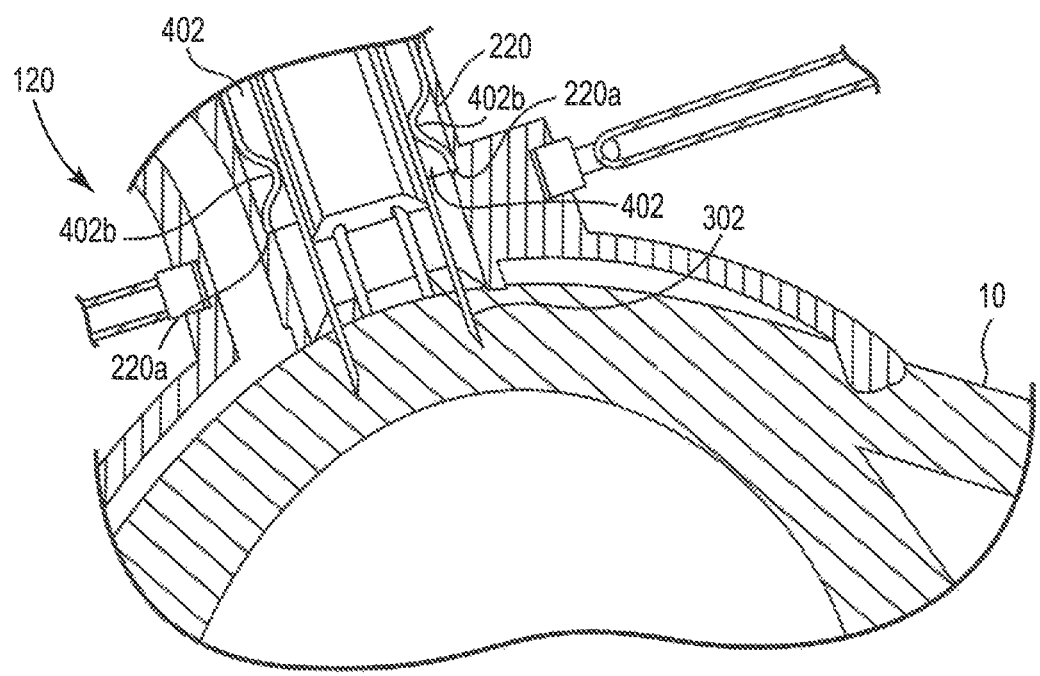

With continued reference to FIG. 7, channel 220 further includes a radial ledge 220a against which an end of an exterior portion of outer wall 402 is being pressed. Thus, when compression slider 260 is operated to push distal end 408 of compression sleeve 400 toward base 154, the exterior portion of outer wall 402 is held axially in place by radial ledge 220a and compressible or flexible portion 402b of outer wall 402 will buckle radially inward toward an interior wall of channel 220. This radial buckling is illustrated in FIG. 9, which is a sectional view of positioning device 120. Because inner section 406 of compression sleeve 400 is preferably compressible or open, and rigid section 402a of compression sleeve 400 is relatively incompressible both axially and radially, this inward buckling moves needle 302 radially inward toward an inner wall of channel 220.

Figure 8:
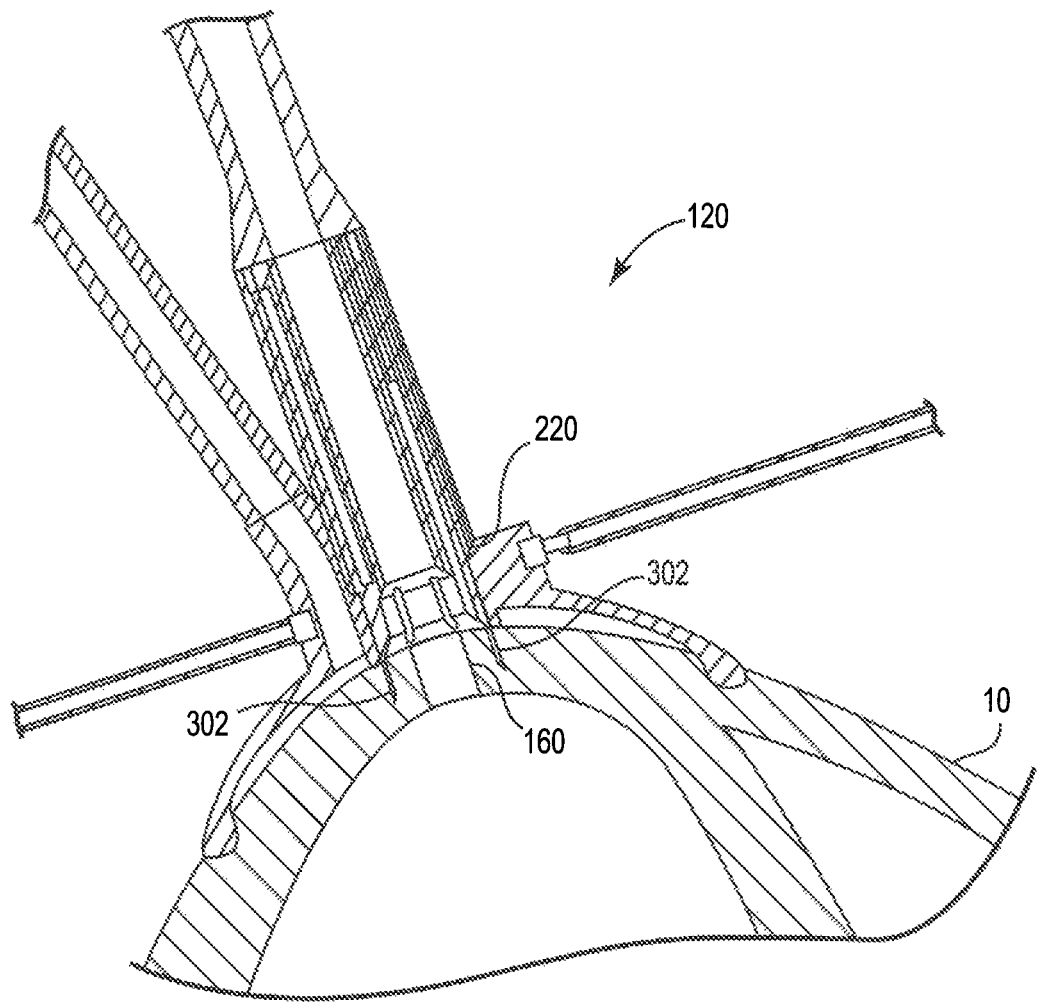
FIGS. 8, 9 and 10 are sectional views of the positioning device shown in FIG. 4 that illustrate exemplary steps of a method for closing an entry point in a ventricle of a heart implementing the closure mechanism shown in FIG. 5.
Figure 10:
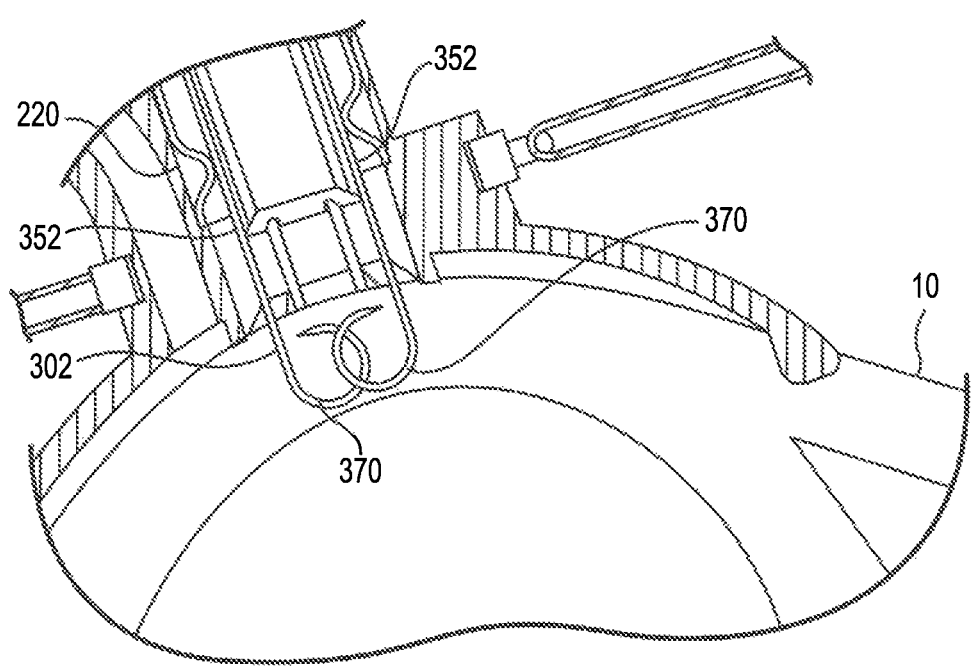
Figure 14:
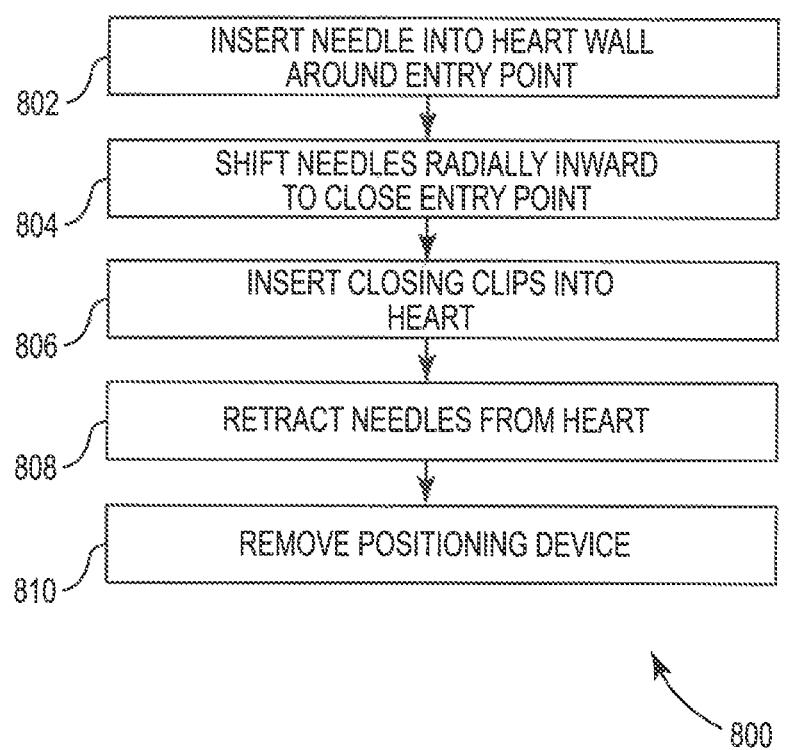
FIG. 14 is a flow chart illustrating one embodiment of a method of closing an entry point into a ventricle of a heart, in accordance with the invention.

An exemplary method of closing an entry point 160 in accordance with one embodiment of the invention will be explained with reference to FIGS. 8, 9 and 10, each of which is a sectional view illustrating positioning device 120 as it can be deployed at the apex of a heart 10, and FIG. 14, which is a flowchart depicting such an exemplary method 800. In particular, this method is directed to the situation that occurs after deploying and carrying out a procedure using positioning device 120 (as discussed above with respect to positioning device 120) for closing the entry point 160. To accomplish this, after retracting any implements used to carry out a procedure in heart 10 (e.g., surgical procedures that are performed via a device inserted through the first access valve 24), needle insertion slider 250 (shown in FIG. 4) can be axially slid towards heart 10 to insert needles 302 partially into the wall of heart 10 in positions that are radially exterior to entry point 160, as in step 802. At this stage, compression slider 260 can be operated to slide a distal end 408 of compression sleeve 400 towards heart 10, as described in step 804 and as is shown in FIG. 9. As discussed above, this has the effect of causing a flexible portion 402b of outer wall 402 to buckle, thereby moving needles 302 radially inward toward an inner wall of a channel, such as channel 220. In this way, the portions of needles 302 inside the wall of heart 10 will radially squeeze entry point 160 toward a closed condition. Next, push-rod slider 240 can be slid axially towards heart 10 to push clips 370 into wall of heart 10, as depicted in step 806 and as is shown in FIG. 10, which may occur simultaneously and/or serially. Needle insertion slider 250 can then be operated to retract needles 302 from the wall of heart 10, as in step 808.

Clips 370, which are visible in FIG. 10, may be self-closing or forming clips and may be formed of a shape memory type of material, such as Nitinol, for example. Such self-closing clips may have a predetermined "u", circular, semi-circular, coil, partial coil, or other shape. In general, an embodiment of the self-closing clips used in accordance with the invention may have a closed memory set configuration which is transitionable from a natural or undeformed state to a biased, deformed, or deflected state, which can then revert back to the natural or undeformed state, such as when external forces are removed from the clip. The self-closing clip can exhibit a loop-shaped memory set shape or configuration. The shape memory member can be Nitinol wire and provided with a desired memory set configuration to exhibit pseudo elastic (super elastic) behavior. In other words, at least a portion of the shape memory alloy is converted from its austenitic phase to its martensitic phase when the wire is in its deformed configuration. As the stress is removed, the material undergoes a martensitic to austenitic conversion and springs back (e.g., self-reverts) to its original or undeformed or undeflected configuration. Additional examples of self-closing clips useful with the present disclosure are described in U.S. Pat. No. 6,607,541, entitled "Tissue Connector Apparatus and Methods"; U.S. Pat. No. 6,641,593, entitled "Tissue Connector Apparatus and Methods"; U.S. Pat. No. 6,613,059, entitled "Tissue Connector Apparatus and Methods"; and U.S. application Ser. No. 10/646,254 filed Aug. 22, 2003 and entitled "Surgical Connection Apparatus and Methods"; the teachings of which are each incorporated herein by reference in their entireties.

In accordance with one embodiment of the invention, as clips 370 are moved axially out of needles 302, clips 370 preferably tunnel radially across entry point 160 and axially down a side opposite from an entry side. In this way, each clip 370 can cross another clip 370. Because this embodiment includes one clip housed in each needle 302, if there are six needles 302 used with a needle assembly 300, six clips will be circumferentially spaced around closed entry point 160. After closing entry point 160, suction can be removed from any vacuum supplies (e.g., vacuum supply 140), any sutures can be removed, and positioning device 120 can be removed, as is described in step 819.

Figure 11:
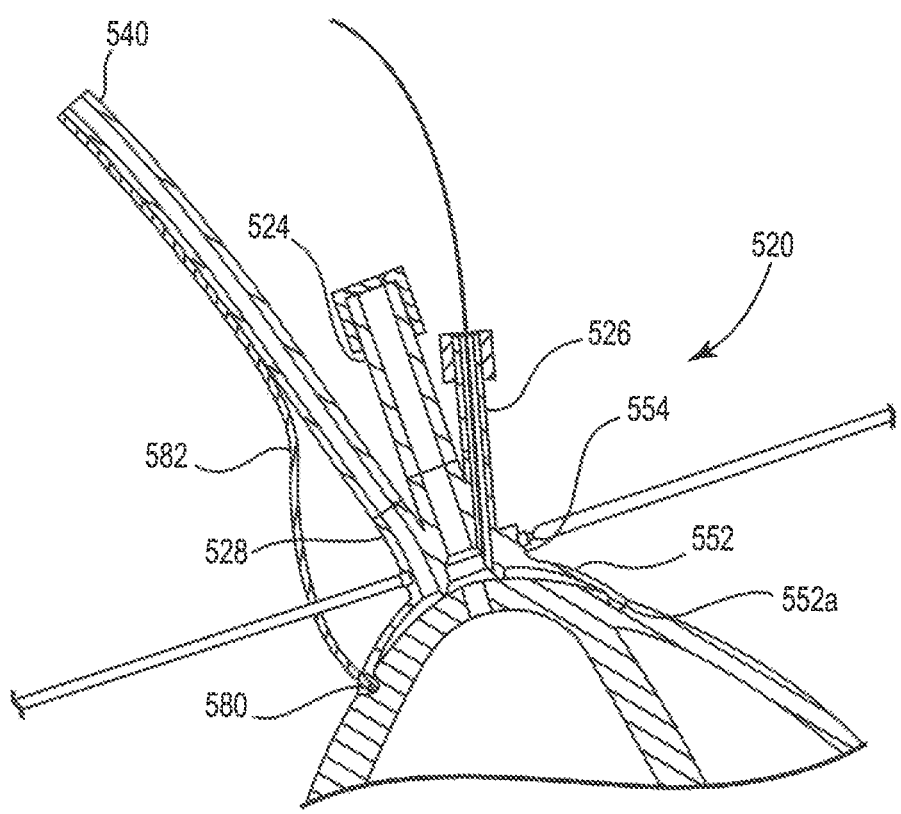
FIG. 11 is a sectional view of another embodiment of a positioning device for providing apical heart access including a sensor in accordance with the invention.

FIG. 11 is a sectional view of another embodiment of a positioning device 520 in accordance with the invention. Similar to positioning device 20 shown in FIGS. 1 and 2, positioning device 520 includes a cylindrical base 554 located in a central region of a circular suction cup 552. Positioning device 520 also includes a primary access valve 524, a secondary access valve 526 and a vacuum port 528, each of which extends from base 554. Vacuum port 528 can be connected at its distal end with a vacuum supply tube 540. Positioning device 520 additionally includes a sensor 580 at the distal end of a sensing lead 582. Sensing lead 582 is shown as extending generally along the length of the vacuum supply tube 540; however, one or more sensing leads 582 could instead be positioned in one or more different locations relative to the positioning device 520. Sensor 580 could, for example, be positioned and used to monitor aspects of heart 10 during a procedure carried out thereon using positioning device 520. In the embodiment of FIG. 11, the sensor 580 is located at an outer rim 552a of suction cup 552, though sensor 580 could also be located at other locations on positioning device 520.

Figure 12A:
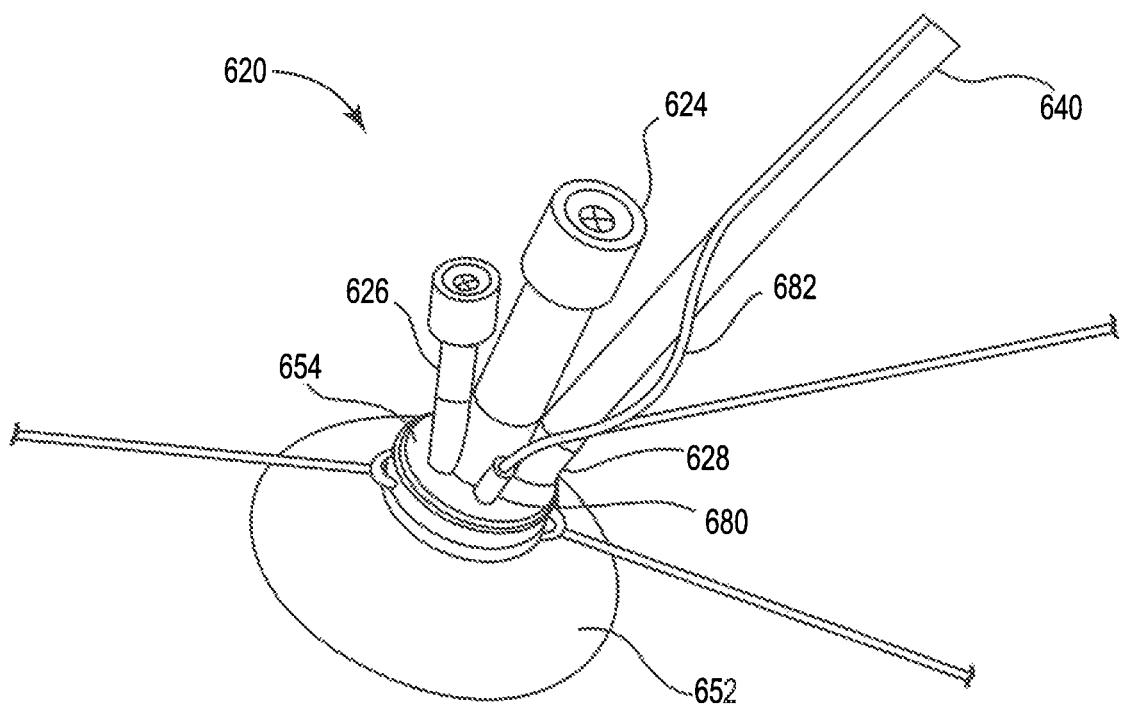
FIGS. 12A and 12B are top and bottom oblique views of yet another embodiment of a positioning device for providing apical heart access in accordance with the invention, which includes a lighting device.
Figure 12B:
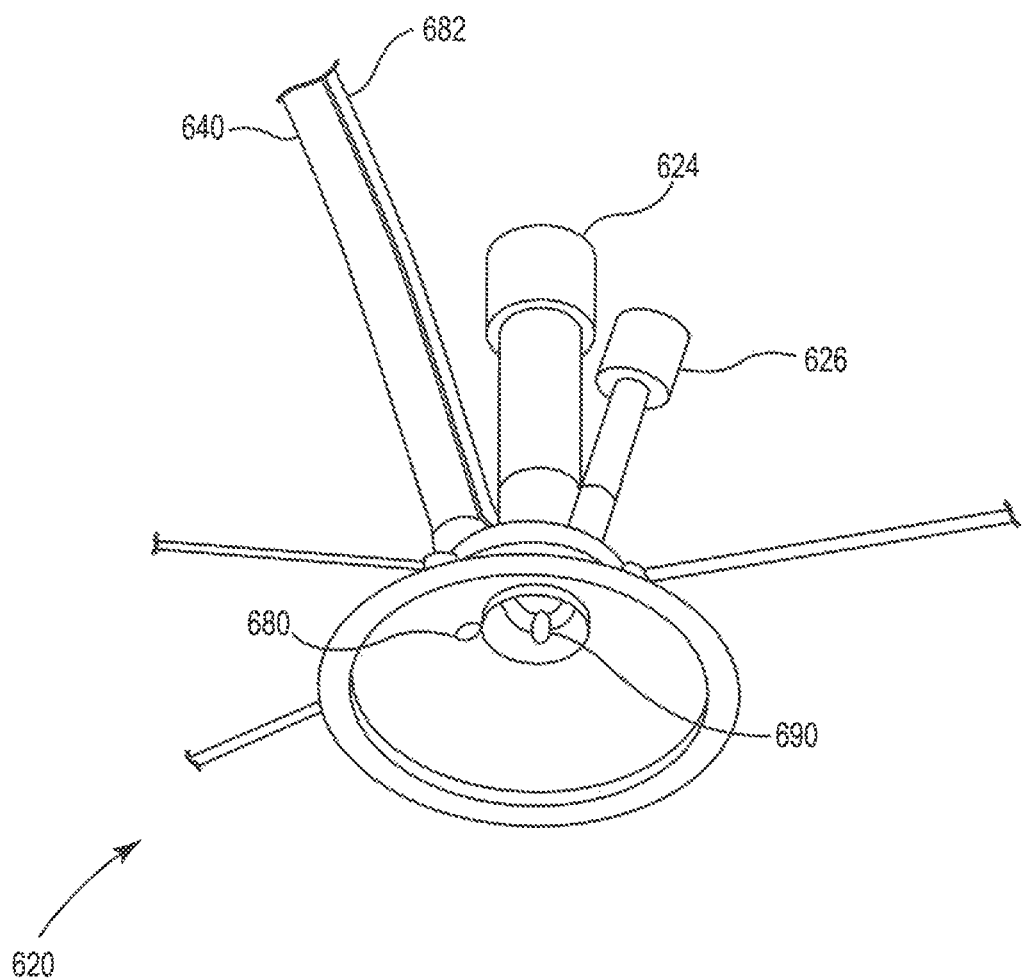

FIGS. 12A and 12B are top and bottom oblique views of another embodiment of a positioning device 620 in accordance with the invention. Similar to positioning device 20, positioning device 620 includes a cylindrical base 654 located in a central region of a circular suction cup 652. Positioning device 620 also includes a primary access valve 624 and a secondary access valve 626 extending from base 654. Additionally, a vacuum port 628 extends from base 654 for interconnecting with a vacuum supply tube 640. Positioning device 620 additionally includes a port 680 in base 654 that passes through to an interior region of suction cup 652. Port 680 can have an LED or other lighting device passing through it, which can be provided with power via a power cable 682, for example. FIG. 12A illustrates one exemplary position of the power cable 682 in which it is routed along vacuum supply tube 640; however, it is understood that the positioning device 620 may include one or more power cables 682 in different and/or additional locations to provide power to one or more additional LED or other lighting or visualization devices, for example. FIG. 12B illustrates one exemplary position of an LED light 690 as being near the opening of primary access valve 624 so that it can thereby be used to provide better visualization of some type of device, such as a surgical device, when it is inserted through the access valve 624 and into the heart.

Additionally, drugs or other fluids can be administered to a specific part of the patient's anatomy through access devices provided with the positioning devices of the invention. For example, a drug could be administered into a heart ventricle by a device, such as introducer 85 (see FIG. 3B) that is shown as positioned within access valve 24, but which could alternatively or additionally be positioned within other access components, such as access valve 26 (see FIG. 3B, for example) or access valve 200 (see FIG. 4, for example). In yet another alternative, a drug or other fluid could be inserted directly into the access valve (i.e., without any type of introducer or other tubular device). The drug or fluid delivery can occur either before entering the left ventricle, in preparation of an initial incision (e.g., a vaso-restrictor to reduce blood flow), or after completion of procedure, such as a clotting agent that can be used to reduce blood loss.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

What is claimed is:

1. A positioning device for providing access to a ventricle of a heart, the positioning device comprising:
    a suction cup positionable over an apex of the heart, wherein the cup includes a vacuum port;
    at least a first hemostatic access valve coupled to the suction cup for accessing an entry point to the ventricle of the heart, the first hemostatic access valve having a channel open to an interior of the suction cup and having a distal end accessible outside a patient; and
    at least one fastening mechanism coupled to the suction cup, the fastening mechanism having at least one attachment element on a surface of the fastening mechanism, wherein the fastening mechanism is rotatable about a longitudinal axis of the suction cup when the suction cup is fastened to the heart.

2. The positioning device of claim 1, wherein the attachment element comprises a suture attachment for attaching guide sutures to the fastening mechanism.

3. The positioning device of claim 1, further comprising a second hemostatic access valve.

4. The positioning device of claim 1, further comprising a sensor coupled to the suction cup.

5. The positioning device of claim 1, further comprising a light coupled to the suction cup.

6. The positioning device of claim 1, wherein the fastening mechanism is independently rotatable about the longitudinal axis of the cup.

7. A positioning device for providing access to a ventricle of a heart, the positioning device comprising:
    a suction cup positionable over an apex of the heart, wherein the suction cup defines,
        a first interior section located to access an entry point to the ventricle and
        a second interior section separated from the first section by a rim protruding from an interior surface of the suction cup, wherein only the second interior section is in communication with a vacuum port of the suction cup for providing suction to secure the positioning device to the heart; and a first access valve in communication with the first interior section of the suction cup for accessing the entry point to the ventricle, the first access valve having a channel open to the first interior section of the suction cup and having a distal end accessible outside a patient.

8. The positioning device of claim 7, wherein the second interior section is formed concentrically around the first interior section.

9. The positioning device of claim 7, further comprising a second access valve in communication with the first interior section.

10. The positioning device of claim 7, wherein channel of the first access valve comprises at least one clip.

11. The positioning device of claim 10, wherein the at least one clip is housed in at least one needle in the channel.

12. The positioning device of claim 11, wherein the first access valve comprises:
    a first control for placing the at least one needle into a heart wall; and
    a second control for placing the at least one clip into the heart wall.

13. The positioning device of claim 12, wherein the first access valve further comprises:
    a third control; and
    a compression sleeve coupled to the third control, wherein the third control controls compression of the compression sleeve to cause the at least one needle to shift radially inward.

14. The positioning device of claim 10, wherein the at least one clip comprises a self-closing clip.

15. The positioning device of claim 14, wherein the self-closing clip comprises a shape-memory material.

16. A method of accessing a ventricle of the heart comprising the steps of:
    placing a cup portion of a positioning device at the apex of the heart;
    forming an entry point into a ventricle of the heart through a first valve in the cup portion of the positioning device;
    accessing the ventricle of the heart through the first valve and entry point;
    inserting at least one needle in a first location of a heart wall radially spaced from the entry point, wherein the at least one needle pierces the heart wall;
    shifting the at least one needle radially inward to push the entry point toward a closed position;
    inserting at least one clip into a second location of the heart wall radially spaced from the entry point to hold the entry point in the closed position; and
    removing the at least one needle from the heart wall.

17. The method of claim 16, wherein placing a cup portion of the positioning device at the apex of the heart comprises securing the cup portion of the positioning device at the apex of the heart.

18. The method of claim 17, wherein placing a cup portion of the positioning device at the apex of the heart further comprises attaching guide sutures from intercostal locations to the positioning device.

19. The method of claim 17, further comprising the step of introducing a drug into a ventricle of the heart through the first valve of the positioning device.

\* \* \* \* \*